US012803309B2

(12) United States Patent
Shi

(10) Patent No.: US 12,803,309 B2
(45) Date of Patent: Nov. 17, 2026

(54) DETECTOR BOX

(71) Applicant: SHANGHAI UNITED IMAGING HEALTHCARE CO., LTD., Shanghai (CN)

(72) Inventor: Bo Shi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 874 days.

(21) Appl. No.: 18/190,056

(22) Filed: Mar. 24, 2023

(65) Prior Publication Data

US 2023/0238813 A1 Jul. 27, 2023

Related U.S. Application Data

(63) Continuation of application No. PCT/CN2021/120435, filed on Sep. 24, 2021.

(30) Foreign Application Priority Data

Sep. 24, 2020 (CN) ......................... 202022121226.0
Sep. 24, 2020 (CN) ......................... 202022124649.8

(51) Int. Cl.
*H02J 7/00* (2026.01)
*A61B 6/42* (2024.01)
*H02J 7/70* (2026.01)

(52) U.S. Cl.
CPC ............ *H02J 7/751* (2026.01); *A61B 6/4283* (2013.01); *A61B 6/4233* (2013.01)

(58) Field of Classification Search
None
See application file for complete search history.

(56) References Cited

U.S. PATENT DOCUMENTS

| | | | |
|---|---|---|---|
| 10,185,358 B1 | 1/2019 | Bataller | |
| 2012/0045037 A1 | 2/2012 | Carmichael et al. | |
| 2012/0194132 A1 | 8/2012 | Ikegame | |
| 2012/0281817 A1* | 11/2012 | McBroom ................ | A61B 6/56 378/204 |
| 2013/0064351 A1 | 3/2013 | Urbon et al. | |

FOREIGN PATENT DOCUMENTS

| | | |
|---|---|---|
| CH | 705314 A2 | 1/2013 |
| CN | 204600509 U | 9/2015 |

(Continued)

OTHER PUBLICATIONS

The Extended European Search Report in European Application No. 21871617.3 mailed on Jan. 23, 2024, 10 pages.

(Continued)

*Primary Examiner* — Arun C Williams
(74) *Attorney, Agent, or Firm* — METIS IP LLC

(57) ABSTRACT

A device may include a housing including an accommodating cavity and an insertion opening configured to allow insertion of a detector into the accommodating cavity. The device may also include a locking mechanism configured to prevent the detector from leaving the accommodating cavity. The device may also include a charging assembly arranged on the housing. The charging assembly may include a charging head and an elastic element configured to drive the charging head away from a charging port of the detector.

20 Claims, 7 Drawing Sheets

500

(56) References Cited

FOREIGN PATENT DOCUMENTS

| | | | |
|---|---|---|---|
| CN | 105982680 | A | 10/2016 |
| CN | 105982681 | A | 10/2016 |
| CN | 205612483 | U | 10/2016 |
| CN | 206498218 | U | 9/2017 |
| CN | 111030242 | A | 4/2020 |
| CN | 211556933 0 | | 9/2020 |
| CN | 112006664 | A | 12/2020 |
| CN | 213074801 | U | 4/2021 |
| CN | 213243590 | | 5/2021 |

OTHER PUBLICATIONS

International Search Report in PCT/CN2021/120435 mailed on Jan. 6, 2022, 5 pages.

Written Opinion in PCT/CN2021/120435 mailed on Jan. 6, 2022, 6 pages.

* cited by examiner

DETECTOR BOX

CROSS-REFERENCE TO RELATED APPLICATIONS

This application is a continuation of International Application No. PCT/CN2021/120435, filed on Sep. 24, 2021, which claims priority to Chinese Application No. 202022124649.8 and Chinese Application No. 202022121226.0, both filed on Sep. 24, 2020, the entire contents of each of which are hereby incorporated by reference.

TECHNICAL FIELD

The present disclosure relates to protection of a flat panel detector, and in particular, to a detector box for protecting a flat panel detector, and/or a mobile X-ray device provided with the detector box.

BACKGROUND

A mobile X-ray device is usually equipped with a flat panel detector, which can meet the imaging needs of various occasions and is flexible in application. Conventionally, the flat panel detector may be protected by a detector box. The detector box may be a box-like structure made of plastic or rubber with certain elasticity. Under the action of an external force, the detector box may be deformed appropriately, so that the flat panel detector can be directly clamped in the detector box. However, the detector box is inconvenient to use. It is desirable to provide a convenient device for protecting a flat panel detector.

SUMMARY

An aspect of the present disclosure provides a device. The device may include a housing including an accommodating cavity and an insertion opening configured to allow insertion of a detector into the accommodating cavity. The device may also include a locking mechanism configured to prevent the detector from leaving the accommodating cavity. The device may also include a charging assembly arranged on the housing. The charging assembly may include a charging head and an elastic element configured to drive the charging head away from a charging port of the detector.

In some embodiments, the locking mechanism may be arranged on one end of the insertion opening. A locking block may be arranged on a first end of the locking mechanism close to the insertion opening, and a second end of the locking mechanism away from the insertion opening may be configured to be lockable, so that the locking block has a locked state that prevents the detector from leaving the accommodating cavity.

In some embodiments, the locking mechanism may include a driving rod and a locking assembly. The driving rod may be rotatably connected to the housing via a rotating shaft. The locking block may be arranged on a first end of the driving rod, and a locking groove may be arranged on a second end of the driving rod. The locking assembly may have a locked state in which the locking groove is connected with the locking assembly and an unlocked state in which the locking assembly is separated from the locking groove.

In some embodiments, the locking assembly may include a telescopic shaft and a driving component, and the driving component may be configured to drive the telescopic shaft to move close to or away from the locking groove.

In some embodiments, the driving component may include: a magnetic element configured to drive the telescopic shaft to move away from the locking groove when the magnetic element is energized; and a first elastic member. One end of the first elastic member may be connected with the telescopic shaft. The first elastic member may be configured to drive the telescopic shaft to move close to the locking groove when the magnetic element is powered off.

In some embodiments, the locking assembly may include a supporting frame. The supporting frame may be arranged on the housing. The second end of the driving rod may be located closer to the supporting frame than the first end of the driving rod. The magnetic element may be arranged inside the supporting frame. A hole may be arranged on a wall of the supporting frame. The telescopic shaft movably may go through the hole. A first end of the first elastic member may be connected to the wall, and a second end of the first elastic member may be connected to the telescopic shaft.

In some embodiments, the locking mechanism may include a second elastic member, a first end of the second elastic member may be connected to the housing, and a second end of the second elastic member may be connected to the driving rod, so that the locking block has an initial state that allows the detector to leave the accommodating cavity.

In some embodiments, the second end of the second elastic member may be connected to a portion of the driving rod between the rotating shaft and the locking groove to tighten the second end of the driving rod away from the locking block, so that the locking block is driven to move away from the detector.

In some embodiments, the second end of the second elastic member may be connected to a portion of the driving rod between the rotating shaft and the locking block to drive the locking block to move away from the detector.

In some embodiments, a limit component may be disposed in the accommodating cavity and configured to limit a distance between the locking block and the detector when the locking block is in the initial state.

In some embodiments, the device may include a panel connected to a first end of the housing. The housing may have a closed state in which the housing is in contact with the panel and an open state in which the housing is angled to the panel. The device may also include a driving unit arranged on the panel, the driving unit may be configured to drive the charging head to overcome an elastic force of the elastic element to move into the accommodating cavity and be plugged into the charging port when the housing is switched from the open state to the closed state.

In some embodiments, the charging assembly may include a charging base and a movable base. A charging opening may be arranged on the charging base and opposite to the charging port. The movable base may be opposite to the charging base, the elastic element may be arranged between the charging base and the movable base. The charging head may be connected to the movable base. The movable base may be configured to drive, under an action of the driving unit, the charging head to be plugged into the charging port through the charging opening.

In some embodiments, the charging assembly may include a guiding component configured to guide a movement of the movable base relative to the charging base.

In some embodiments, the driving unit may be provided with a driving inclined surface abutting against the movable base.

In some embodiments, a guide roller may be rotatably arranged on the movable base. The driving inclined surface may abut against the guide roller.

In some embodiments, the guide roller may include a plurality of guide members arranged on the movable base at intervals. The driving unit may include a plurality of driving elements, and each of the plurality of guide members may correspond to one of the plurality of driving elements.

In some embodiments, the movable base may be provided with a guiding inclined surface, the driving inclined surface of the driving unit abutting against the guiding inclined surface.

In some embodiments, a first attraction element may be arranged on the panel, and a second attraction element may be arranged on the housing. The first attraction element and the second attraction element may be attracted together when the housing is in the closed state.

In some embodiments, the first attraction element and the second attraction element may be magnets; or one of the first attraction element and the second attraction element may be metal, and another of the first attraction element and the second attraction element may be a magnet; or the first attraction element and the second attraction element may be electromagnets, induction switches may be arranged on the electromagnets, and the induction switches may be configured to de-energize the electromagnets when an object is detected.

In some embodiments, a limit mechanism may be arranged between the housing and the panel, and the limit mechanism may be configured to limit an angle between the panel and the housing in the open state.

In some embodiments, the limit mechanism may include a movable rod and a rod base. The rod base may be arranged on the housing. A first end of the movable rod may be rotatably connected to the panel, and a second end of the movable rod may be connected to the rod base.

In some embodiments, the detector may include a flat panel detector in a mobile X-ray device, the detector may be configured to detect X-rays.

Another aspect of the present disclosure provides a device. The device may include a detector; and a detector box configured to accommodate the detector. The detector box may include: a housing including an accommodating cavity and an insertion opening configured to allow insertion of a detector into the accommodating cavity; a locking mechanism configured to prevent the detector from leaving the accommodating cavity; and a charging assembly arranged on the housing. The charging assembly may include a charging head and an elastic element configured to drive the charging head away from a charging port of the detector.

Yet another aspect of the present disclosure provides a mobile X-ray device. The device may include an X-ray source configured to emit X-rays; a detector configured to detect the X-rays; and a detector box configured to accommodate the detector. The detector box may include: a housing including an accommodating cavity and an insertion opening configured to allow insertion of a detector into the accommodating cavity; a locking mechanism configured to prevent the detector from leaving the accommodating cavity; and a charging assembly arranged on the housing. The charging assembly may include a charging head and an elastic element configured to drive the charging head away from a charging port of the detector.

Yet another aspect of the present disclosure provides a device. The device may include a housing including an accommodating cavity and an insertion opening configured to allow insertion of a detector into the accommodating cavity; a panel connected to a first end of the housing; a charging assembly arranged on the housing; a driving unit arranged on the panel. The driving unit may be configured to drive the charging head to overcome an elastic force of the elastic element to move into the accommodating cavity and be plugged into the charging port when the housing is switched from the open state to the closed state. The housing may have a closed state in which the housing is in contact with the panel and an open state in which the housing is angled to the panel. The charging assembly may include a charging head and an elastic element configured to drive the charging head away from a charging port of the detector.

In some embodiments, the charging assembly may include a charging base and a movable base. A charging opening may be arranged on the charging base and opposite to the charging port. The movable base may be opposite to the charging base, the elastic element may be arranged between the charging base and the movable base. The charging head may be connected to the movable base. The movable base may be configured to drive, under an action of the driving unit, the charging head to be plugged into the charging port through the charging opening.

In some embodiments, the charging assembly may include a guiding component configured to guide a movement of the movable base relative to the charging base.

In some embodiments, the driving unit may be provided with a driving inclined surface abutting against the movable base.

In some embodiments, a guide roller may be rotatably arranged on the movable base, the driving inclined surface abutting against the guide roller.

In some embodiments, the guide roller may include a plurality of guide members arranged on the movable base at intervals. The driving unit may include a plurality of driving elements, each of the plurality of guide members corresponding to one of the plurality of driving elements.

In some embodiments, the movable base may be provided with a guiding inclined surface, the driving inclined surface abutting against the guiding inclined surface.

In some embodiments, a first attraction element may be arranged on the housing, and a second attraction element may be arranged on the panel. The first attraction element and the second attraction element may be adsorbed together when the housing is in the closed state.

In some embodiments, the first attraction element and the second attraction element may be magnets; or one of the first attraction element and the second attraction element may be metal, and another of the first attraction element and the second attraction element may be a magnet; or the first attraction element and the second attraction element may be electromagnets, induction switches may be arranged on the electromagnets, and the induction switches may be configured to de-energize the electromagnets when an object is detected.

In some embodiments, a limit mechanism may be arranged between the housing and the panel, and the limit mechanism may be configured to limit an angle between the panel and the housing in the open state.

In some embodiments, the limit mechanism may include a movable rod and a rod base. The rod base may be arranged on the housing. A first end of the movable rod may be rotatably connected to the panel, and a second end of the movable rod may be connected to the rod base.

Yet another aspect of the present disclosure provides a device. The device may include a detector; and a detector box configured to accommodate the detector. The detector box may include: a housing including an accommodating cavity and an insertion opening configured to allow insertion of a detector into the accommodating cavity; a panel connected to a first end of the housing; a charging assembly arranged on the housing; a driving unit arranged on the panel. The driving unit may be configured to drive the charging head to overcome an elastic force of the elastic element to move into the accommodating cavity and be plugged into the charging port when the housing is switched from the open state to the closed state. The housing may have a closed state in which the housing is in contact with the panel and an open state in which the housing is angled to the panel. The charging assembly may include a charging head and an elastic element configured to drive the charging head away from a charging port of the detector.

Yet another aspect of the present disclosure provides a mobile X-ray device. The device may include: an X-ray source configured to emit X-rays; a detector configured to detect the X-rays; and a detector box configured to accommodate the detector. The detector box may include: a housing including an accommodating cavity and an insertion opening configured to allow insertion of a detector into the accommodating cavity; a panel connected to a first end of the housing; a charging assembly arranged on the housing; a driving unit arranged on the panel. The driving unit may be configured to drive the charging head to overcome an elastic force of the elastic element to move into the accommodating cavity and be plugged into the charging port when the housing is switched from the open state to the closed state. The housing may have a closed state in which the housing is in contact with the panel and an open state in which the housing is angled to the panel. The charging assembly may include a charging head and an elastic element configured to drive the charging head away from a charging port of the detector.

Yet another aspect of the present disclosure provides a device. The device may include a housing including an accommodating cavity and an insertion opening configured to allow insertion of a detector into the accommodating cavity; a locking mechanism configured to prevent the detector from leaving the accommodating cavity and arranged on one end of the insertion opening, wherein: a locking block may be arranged on a first end of the locking mechanism close to the insertion opening, and a second end of the locking mechanism away from the insertion opening may be configured to be lockable, so that the locking block has a locked state that prevents the detector from leaving the accommodating cavity.

In some embodiments, the locking mechanism may include a driving rod and a locking assembly, wherein:

- the driving rod may be rotatably connected to the housing via a rotating shaft;
- the locking block may be arranged on a first end of the driving rod, and a locking groove may be arranged on a second end of the driving rod; and
- the locking assembly may be configured to have a locked state in which the locking groove is fixed with the locking assembly and an unlocked state in which the locking assembly is separated from the locking groove.

In some embodiments, the locking assembly may include a telescopic shaft and a driving component, and the driving component may be configured to drive the telescopic shaft to move close to or away from the locking groove.

In some embodiments, the driving component may include: a magnetic element configured to drive the telescopic shaft to move away from the locking groove when the magnetic element is energized; and a first elastic member. One end of the first elastic member may be connected with the telescopic shaft, and the first elastic member may be configured to drive the telescopic shaft to move close to the locking groove when the magnetic element is powered off.

In some embodiments, the locking assembly may include a supporting frame, wherein:

- the supporting frame may be arranged on the housing, and the second end of the driving rod may be located closer to the supporting frame than the first end of the driving rod;
- the magnetic element may be arranged inside the supporting frame;
- a hole may be arranged on a wall of the supporting frame, and the telescopic shaft movably may go through the hole; and
- a first end of the first elastic member may be connected to the wall, and a second end of the first elastic member may be connected to the telescopic shaft.

In some embodiments, the locking mechanism may include a second elastic member, a first end of the second elastic member may be connected to the housing, and a second end of the second elastic member may be connected to the driving rod, so that the locking block has an initial state that allows the detector to leave the accommodating cavity.

In some embodiments, the second end of the second elastic member may be connected to a portion of the driving rod between the rotating shaft and the locking groove to tighten the second end of the driving rod away from the locking block, so that the locking block is driven to move away from the detector.

In some embodiments, the second end of the second elastic member may be connected to a portion of the driving rod between the rotating shaft and the locking block to drive the locking block to move away from the detector.

In some embodiments, a limit component may be disposed in the accommodating cavity and configured to limit a distance between the locking block and the detector when the locking block is in the initial state.

Yet another aspect of the present disclosure provides a device. The device may include a detector; and a detector box configured to accommodate the detector. The detector box may include: a housing including an accommodating cavity and an insertion opening configured to allow insertion of a detector into the accommodating cavity; a locking mechanism configured to prevent the detector from leaving the accommodating cavity and arranged on one end of the insertion opening, wherein: a locking block may be arranged on a first end of the locking mechanism close to the insertion opening, and a second end of the locking mechanism away from the insertion opening may be configured to be lockable, so that the locking block has a locked state that prevents the detector from leaving the accommodating cavity.

Yet another aspect of the present disclosure provides a mobile X-ray device. The device may include an X-ray source configured to emit X-rays; a detector configured to detect the X-rays; and a detector box configured to accommodate the detector. The detector box may include: a housing including an accommodating cavity and an insertion opening configured to allow insertion of a detector into the accommodating cavity; a locking mechanism configured to prevent the detector from leaving the accommodating cavity and arranged on one end of the insertion opening, wherein: a locking block may be arranged on a first end of the locking mechanism close to the insertion opening, and a second end of the locking mechanism away from the insertion opening may be configured to be lockable, so that the locking block has a locked state that prevents the detector from leaving the accommodating cavity.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
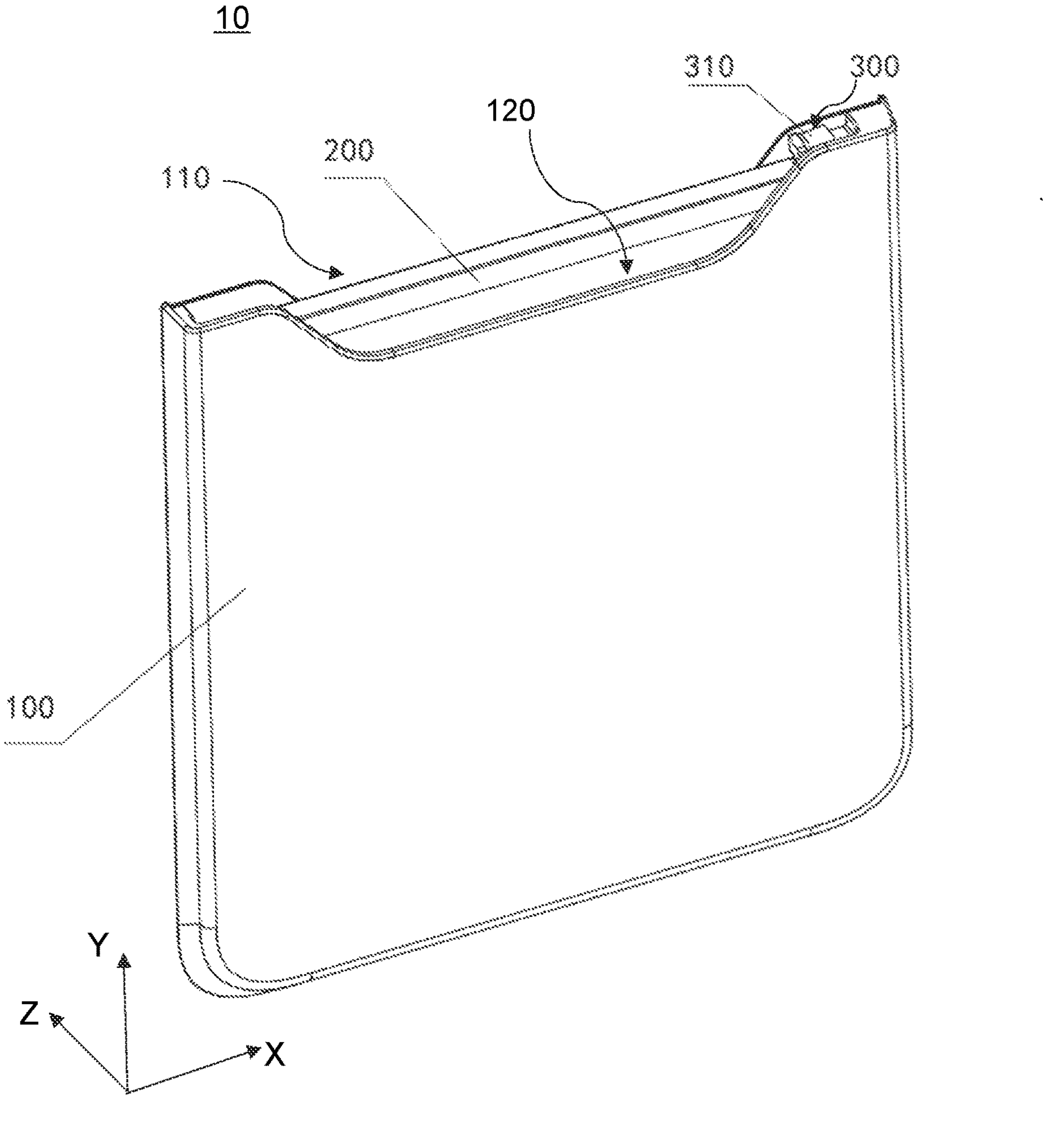
FIG. 1 is a schematic diagram illustrating an exemplary detector box according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "top," "bottom," "inside," "outside," "middle," "center", "upper", "lower", "left", "right", "vertical", "horizontal", "inner", "outer", etc. for indicating an orientation or a positional relationship are based on orientations or positional relationships shown in the drawings, which is only for the convenience of describing the present disclosure, and does not indicate or imply that the devices or elements must have a specific orientation, therefore it cannot be understood as a limitation of the present disclosure. In addition, the terms "first" and "second" are only used for descriptive purposes, and cannot be understood as indicating or implying relative importance. The terms "first position" and "second position" are two different positions.

It should be noted that, unless otherwise clearly specified and limited, the terms "installation", "installing", "connection", and "connecting" should be understood in a broad sense. For example, the terms can refer to a fixed connection or a detachable connection. As another example, the terms can refer to be a mechanical connection or an electrical connection. As still another example, the terms can refer to a direct connection or an indirect connection through an intermediate medium. As still another example, the terms can refer to a connection between two components. For those skilled in the art, the specific meanings of the above terms in the present disclosure can be understood in specific situations.

A conventional detector box mostly has a box-like structure made of plastic or rubber with certain elasticity. Under the action of an external force, the detector box may be deformed appropriately, so that the detector can be directly clamped in the detector box. The detector box may have a simple structure and an accurate size. If the size of the detector box is slightly larger than the accurate size, the detector cannot be locked, thereby the detector being easily leaving the detector box. If the size of the detector box is slightly smaller than the accurate size, and the detector cannot be clamped in the detector box. Moreover, the assembly of the detector and the detector box with the accurate size is still difficult. Other types of detector boxes, such as a flip-type detector box, have complex structures and large sizes.

An aspect of the present disclosure relates to a device (also referred as to a detector box) for protecting a detector. The device may include a housing, a locking mechanism, and a charging assembly. The housing may include an accommodating cavity and an insertion opening configured to allow insertion of a detector into the accommodating cavity. The locking mechanism may be configured to prevent the detector from leaving the accommodating cavity. The charging assembly may be arranged on the housing. The charging assembly may include a charging head and an elastic element configured to drive the charging head away from a charging port of the detector. Compared with the conventional detector box, the detector box of the present disclosure may accommodate detectors with different sizes, and stably limit the detector inside the detector box to prevent the detector from leaving the detector box. Moreover, the detector box of the present disclosure may have a small size to facilitate to carry.

The detector box of the present disclosure may be configured to protect a detector such as a flat panel detector.

In some embodiments, the detector box may be widely used in various scenarios for protecting a detector. For example, the detector box may be used in indoor or outdoor occasions for protecting a detector. As another example, when a user is carrying a detector, the detector may be placed in the detector box to prevent objects from hitting the detector to protect the detector. In some embodiments, the detector box may be used to charge the detector. For example, when the detector is placed in the detector box, the detector may be automatically plugged into the charging port, so that the detector may be charged. In some embodiments, the detector box may be applied to a mobile X-ray device to place a detector of the mobile X-ray device. For example, when X-ray imaging is not required (e.g., when the mobile X-ray device is moving or a power of the detector is too low), the detector may be placed in the detector box to avoid the detector leaving the mobile X-ray device during the movement of the detector.

Figure 2:
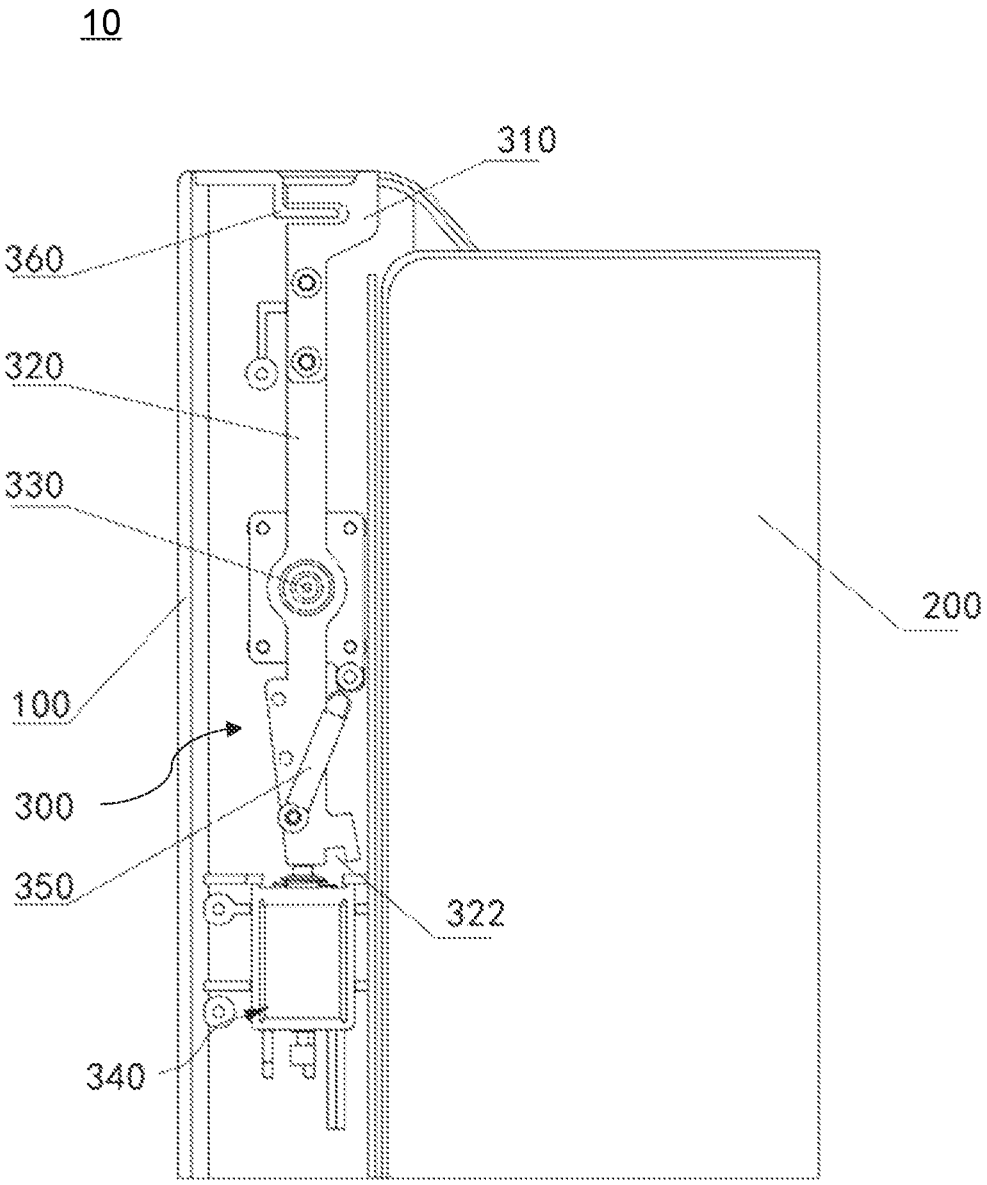
FIG. 2 is a schematic diagram illustrating an exemplary detector box according to some embodiments of the present disclosure.

FIGS. 1 and 2 are schematic diagrams illustrating an exemplary detector box 10 according to some embodiments of the present disclosure. As shown in FIG. 1 and FIG. 2, the detector box 10 may include a housing 100 and a locking mechanism 300.

In some embodiments, the housing 100 may be a main structure for accommodating a detector 200 (e.g., a flat panel detector). Since the detector 200 is generally a cuboid structure, the housing 100 may have a box-shaped structure with a cuboid accommodating cavity. An insertion opening 110 may be arranged on one end of the accommodating cavity along the length direction of the accommodating cavity. Alternatively, the insertion opening 110 may be arranged on one end of the accommodating cavity along the thickness direction or the width direction of the accommodating cavity. The insertion opening 110 may be configured to allow insertion of the detector 200 into the accommodating cavity. In order to facilitate taking out the detector 200 from the accommodating cavity, a downwardly recessed groove 120 may be arranged on the insertion opening 110. A portion of the detector 200 may be exposed outside the groove 120, so that a user may directly control the exposed part of the detector 200 to take the detector 200 out of the accommodating cavity.

In the present disclosure, the X axis, the Y axis, and the Z axis shown in FIG. 1 may form an orthogonal coordinate system. As illustrated, the Y direction (also referred to as the length direction of the accommodating cavity) along the Y axis may refer to a direction in which the detector 200 is moved out of or put into the detector box 10. The X direction (also referred to as the width direction of the accommodating cavity) along the X axis and the Z direction (also referred to as the thickness direction of the accommodating cavity) along the Z axis may be vertical to the Y direction.

In some embodiments, the locking mechanism 300 may be used to limit the detector 200 in the accommodating cavity of the detector box 10 to prevent the detector 200 from leaving the accommodating cavity. In some embodiments, the locking mechanism 300 may be arranged on one end of the insertion opening 110. The locking mechanism 300 may be arranged inside the accommodating cavity or outside the housing 100. In some embodiments, in order to facilitate the installation of the locking mechanism 300 and reduce a volume of the detector box 10, the locking mechanism 300 may be arranged inside the accommodating cavity and located at one end of the accommodating cavity along the width direction (e.g., the Y direction) of the accommodating cavity. In some embodiments, the locking mechanism 300 may be located on the left side or right side (e.g., along the X direction) of the insertion opening 110. That is, the locking mechanism 300 may be located on the left side or right side (e.g., along the X direction) of the detector 200 as shown in FIG. 1, to avoid the interference of the insertion of the detector 200 into the accommodating cavity. In some embodiments, the locking mechanism 300 may include a first end and a second end. The first end of the locking mechanism 300 may be close to the insertion opening 110, and the second end of the locking mechanism 300 may be away from the insertion opening 110. In some embodiments, a locking block 310 may be arranged on the first end of the locking mechanism 300. The second end of the locking mechanism 300 may be configured to be lockable, so that the locking block 310 may have a locked state to prevent the detector 200 from leaving the accommodating cavity. That is, the locking block 310 may press the detector 200 from the top of the detector 200 to apply a pressing force toward the inside of the accommodating cavity to the detector 200, thereby limiting the detector 200 in the accommodating cavity.

In some embodiments, the locking mechanism 300 may be rotatably connected to the housing 100, so that in a rotation process of the locking mechanism 300, the first end of the locking mechanism 300 may move toward the detector 200 and the second end of the locking mechanism 300 may move away from the detector 200. If the second end of the locking mechanism 300 is locked, the locking block 310 disposed on the first end may be pressed against the detector 200. As shown in FIG. 2, in some embodiments, the locking mechanism 300 may include a driving rod 320 and a locking assembly 340. In some embodiments, the driving rod 320 may have a long strip-shaped sheet structure, which may be vertically disposed within the accommodating cavity. For example, the driving rod 320 may be disposed within the accommodating cavity so that the long strip-shaped sheet structure of the driving rod 320 extends along the Y direction. The driving rod 320 may be rotatably connected to the housing 100 via a rotating shaft 330. In some embodiments, a portion of the driving rod 320 between a first end and a second end of the driving rod 320 may be rotatably connected with the housing 100. For example, the middle portion of the driving rod 320 between the first end and the second end of the driving rod may be rotatably connected with the housing 100. In some embodiments, the first end (e.g., an upper end as shown FIG. 2) of the driving rod 320 may be close to the insertion opening 110, and the second end (e.g., a lower end as shown FIG. 2) of the driving rod 320 may be away from the insertion opening 110. In some embodiments, the driving rod 320 may provide with a shaft hole, and the rotating shaft 330 may pass through the shaft hole. The driving rod 320 may be rotatably connected with an inner wall of the accommodating cavity. The inner wall of the accommodating cavity may be a front surface or a rear surface of the accommodating cavity in the thickness direction (e.g., the Z direction) of the accommodating cavity.

As shown in FIG. 2, the locking block 310 may be arranged on the first end (e.g., the upper end) of the driving rod 320 by a connector such as a pin. In some embodiments, the locking block 310 may include a connecting plate and a pressure plate connected with each other at an angle. The connecting plate may be connected to the driving rod 320, and the pressure plate may be configured to press against the detector 200. Alternatively, the locking block 310 and the driving rod 320 may be integrated. In some embodiments, a locking groove 322 may be arranged on the second end (e.g., the lower end) of the driving rod 320. In some embodiments, the locking groove 322 may be a U-groove downward with an opening facing toward the second end of the driving rod 320. The locking assembly 340 may be configured to have a locked state in which the locking groove 322 is fixed with the locking assembly 340 and an unlocked state in which the locking assembly 322 is separated from the locking groove 340. If the locking assembly 340 is in the locked state, the driving rod 320 cannot rotate around the rotating shaft 330, and the position of locking block 310 on the first end of the driving rod 320 may be fixed. If the locking assembly 340 is in an unlocked state, the driving rod 320 may be able to rotate around the rotating shaft 330, and the locking block 310 may move away from the insertion opening 110, so that the detector 200 may be allowed to enter and exit the detector box 10.

Figure 3:
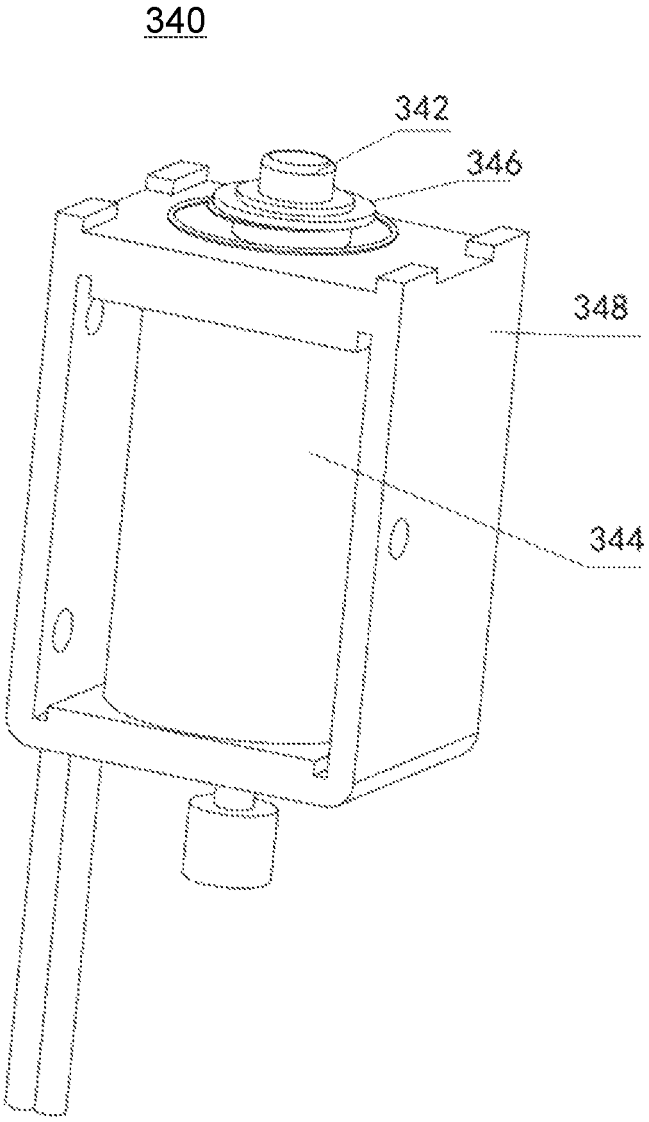
FIG. 3 is a schematic diagram illustrating an exemplary locking assembly according to some embodiments of the present disclosure.

In some embodiments, as shown in FIG. 3, the locking assembly 340 may include a telescopic shaft 342 and a driving component. In some embodiments, the telescopic shaft 342 may have a columnar structure made of a metal material. The telescopic shaft 342 may be connected to the second end of the driving rod 320. The driving component may be configured to drive the telescopic shaft 342 to move close to or away from the locking groove 322. In some embodiments, the driving component may include a magnetic element 344 and a first elastic member 346. The magnetic element 344 may be an electromagnet which has magnetism when it is energized, and loses magnetism when it is powered off. When the magnetic element 344 is energized, the magnetic element 344 may attract the telescoping shaft 342, and drive the telescoping shaft 342 to move away from the driving rod 320 and detach from the locking groove 322. One end of the first elastic member 346 may be connected to the telescopic shaft 342, and another end of the first elastic member 346 may be fixed on the magnetic element 344 or other component (e.g., the supporting frame 348). Alternatively, the first elastic member 346 may be a coil spring. When the magnetic element 344 is energized, the telescopic shaft 342 may be away from the driving rod 320, and the first elastic member 346 may be compressed and has a certain elastic potential energy. When the magnetic element 344 is powered off, the first elastic member 346 may drive the telescopic shaft 342 to move close to the locking groove 340 until the telescopic shaft 342 is engaged with the locking groove 322 to fix the driving rod 320.

In some embodiments, the locking assembly 340 may include a supporting frame 348 to fix the telescopic shaft 342 and the magnetic element 344 in the accommodating cavity. The supporting frame 348 may have a rectangular frame structure formed by a plate member. The supporting frame 348 may be arranged on the housing 100. The second end of the driving rod 320 may be located closer to the supporting frame 348 than the first end of the driving rod 320. The magnetic element 344 may be arranged inside the supporting frame 348. A hole may be arranged on a wall (e.g., as shown in FIG. 2 and FIG. 3, a top wall that is closer to the second end of the driving rod 320) of the supporting frame 348. The telescopic shaft 342 may movably go through the hole. A first end of the first elastic member 346 may be connected to the wall, and a second end of the first elastic member 346 may be connected to the telescopic shaft 342.

In some embodiments, the locking assembly 340 may use other structures to realize movement. For example, the locking assembly 340 may include a motor, a lead screw, and a nut. The motor may be connected with the lead screw for driving the lead screw to rotate. The nut sleeved on the screw may move along the lead screw to realize the engagement or disengagement with the locking groove 322. As another example, the locking assembly 340 may also use an air cylinder as the driving component of the locking assembly 340. A cylinder rod of the air cylinder may be connected to the telescopic shaft 342 for driving the telescopic shaft 342 to move, so as to realize the engagement or disengagement of the telescopic shaft 342 and the locking groove 322.

In some embodiments, the locking mechanism 300 may be movably disposed on the housing 100 to change the position of the locking block 310 by a movement of the locking mechanism 300, so that the locking block 310 may have a pressure state against the detector 200 or a separation state from detector 200. For example, a slide rail may be arranged in the accommodating cavity, and the driving rod 320 may be connected to the slide rail. The locking block 310 may be arranged on the first end of the driving rod 32, and a magnet may be arranged on the second end of the driving rod 320. The locking assembly 340 may include a magnetic element 344. When the magnetic element 344 is energized, the magnetic element 344 may attract the magnet, so that the locking block 310 may move towards the second end of the driving rod 320 and press against the detector 200 with the movement of the driving rod 320 towards the second end of the driving rod 320 along the slide rail, thereby limiting the position of the detector 200. A reset elastic member may be disposed between the magnetic element 344 and the magnet. When the magnetic element 344 is powered off, the driving rod 320 may be reset under the action of the reset elastic member, and the locking block 310 may be separated from the detector 200.

In some embodiments, in order to facilitate the placement of the detector 200 in the detector box 10, the locking block may have an initial state that allows the detector 200 to leave the accommodating cavity. As shown in FIG. 2, the locking mechanism 300 may include a second elastic member 350. A first end of the second elastic member 350 may be connected to the housing 100, and a second end of the second elastic member 350 may be connected to the driving rod 320, so that the locking block 310 may have an initial state that allows the detector 200 to leave the accommodating cavity.

In some embodiments, the second end of the second elastic member 350 may be connected to a portion of the driving rod 320 between the rotating shaft 330 and the locking groove 322 to tighten the second end of the driving rod 320 away from the locking block, so that the locking block 310 may be driven to move away from the detector 200 until the locking block 310 leave the insertion opening 110, thereby the detector 200 being allowed to enter and exit the accommodation cavity. Alternatively, the second end of the second elastic member 350 may be connected to a portion of the driving rod 320 between the rotating shaft 330 and the locking block 310 to drive the locking block 310 to move away from the detector 200 until the locking block 310 leave the insertion opening 110, thereby the detector 200 being allowed to enter and exit the accommodation cavity.

In some embodiments, in order to avoid excessive rotation of the second end of the driving rod 320, which may affect the movement of the detector 200 after the second end of the driving rod 320 abuts against the detector 200, a limit component 360 may be disposed in the accommodating cavity.

As shown in FIG. 2, the limit component 360 may be a limit plate arranged on the insertion opening 110. The limit component 360 may have a z-shape, and one end of the limit component 360 may be fixed to the housing 100, and another end of the limit component 360 may have a limit groove. A limit rod may be arranged on the locking block 310. When the locking block 310 moves away from the insertion opening 110, the limit rod may insert into the limit groove to prevent the movement of the locking block 310 and the movement of the second end of the driving rod 320 away from the locking block 310.

In some embodiments, the detector box 10 shown in FIG. 2 is in the initial state. The process of the locking of the detector 200 in the detector box 10 may include the following operations. First, the detector 200 may be inserted into the accommodating cavity of the detector box 10 from the insertion opening 110. Then, the locking block 310 may rotate clockwise by a user, and the driving rod 320 may rotate clockwise synchronously with the locking block 310. The locking groove 322 on the second end of the driving rod 320 may move to the left in FIG. 2 until the locking groove 322 is clamped on the telescopic shaft 342, thereby the driving rod 320 being fixed and the locking block 310 being pressed against the first end of the detector 200. It should be noted that during this process, the magnetic element 344 is powered off.

In some embodiments, the process for taking the detector 200 out from the detector box 10 may include the following operations. First, the magnetic element 344 may be energized and generate a magnetic force, so that the telescopic shaft 342 may move away from the driving rod 320 and be detached from the lock groove 322. Then, under the driving of the second elastic member 350, the driving rod 320 may rotate counterclockwise, and the locking block 310 may move away from the detector 200 until the locking block 310 leaves the insertion opening 110. Finally, the detector 200 may be taken out from the detector box 10 by a user.

In some embodiments, the magnetic element 344 may be connected to an external power source. In a process for taking the detector 200 out from the detector box 10, the external power source may supply power to the magnetic element 344 to make the magnetic element 344 generate a magnetic force. In some embodiments, the external power source may include a battery, a mobile X-ray device, or the like.

In some embodiments, the detector box 10 may include a controller. The controller may be used to obtain an intention of a user to take out the detector 200. The controller may control the locking assembly 340 to be in the unlocked state according to the intention of the user. In some embodiments, the controller may energize the magnetic element 344 according to the intention of the user, so that the locking assembly 340 may be in the unlocked state.

In some embodiments, the controller may include a switch in series between the external power source and the magnetic element 344. For example, the switch may include a micro switch, a rocker switch, a toggle switch, a slide switch, a button switch, a key switch, a point switch, an electromagnetic switch, or the like, or any combination thereof. In some embodiments, when a user needs to take the detector 200 out from the detector box 10, the user may turn on the switch, so that the external power source supplies power to the magnetic element 344, thereby the locking assembly 340 being in the unlocked state.

In some embodiments, the controller can include a sensor. In some embodiments, the sensor may be mounted on the detector box 10 for detecting the intention of the user to take out the detector 200. Exemplary sensors may include an infrared pyroelectric sensor, a photoelectric switch, or the like. For example, the infrared pyroelectric sensor may be disposed on the detector box 10. When the infrared pyroelectric sensor detects a human body (e.g., a hand of a user), the infrared pyroelectric sensor may output a signal to the external power source (e.g., a mobile X-ray device). After the external power source receives the signal, the external power source may energize the magnetic element 344. As another example, both a transmitting end and a receiving end of the photoelectric switch may be disposed on the detector box 10. When the detector 200 needs to be taken out from the detector box 10, a hand of the user may be located between the transmitting end and the receiving end of the photoelectric switch, so that the receiving end of the photoelectric switch cannot receive the beam emitted by the transmitting end. The receiving end of the photoelectric switch may output a signal to the external power source (e.g., a mobile X-ray device). After the external power source receives the signal, the external power source may energize the magnetic element 344.

In some embodiments, exemplary controllers may include a remote control, a smartphone, a tablet computer, a laptop, a smart bracelet, a smart glasses, a smart helmet, a smart watch, or the like, or any combination thereof. In some embodiments, the controller may identify the intention of the user according to the interaction of the user, and transmit a signal to the external power source (e.g., a mobile X-ray device). After the external power source receives the signal, the external power source may energize the magnetic element 344. For example, the controller may be a remote controller. When it is necessary to take the detector 200 out from the detector box 10, a user may press a button of the remote controller, and the remote control may transmit a control command (i.e., representing the intention of the user to take out the detector 200) to the external power source. After the external power source receives the signal, the external power source may energize the magnetic element 344.

Another aspect of the present disclosure provides a detector. The detector may be accommodated and protected using the detector box 10 of the present disclosure. Yet another aspect of the present disclosure provides a mobile X-ray device configured to perform X-ray imaging to an object (e.g., a patient). The mobile X-ray device may include an X-ray source configured to emit X-rays and a detector (e.g., a flat panel detector) configured to receive the X-rays emitted from the X-ray source. The mobile X-ray device may be provided with a detector box 10 of the present disclosure configured to accommodate and protect the detector when the detector is not in a working state. In some embodiments, the mobile X-ray device may include a mobile digital radiography (DR) device, a mobile digital subtraction angiography (DSA) device, or a mobile C-arm device. The size of the accommodating cavity of the detector box may be relatively large, and the detector may be easily entered into the detector box via the insertion opening. Further, after the detector is placed in the detector box, the detector may be locked by a locking mechanism of the detector box, so that the detector cannot leave the accommodating cavity to avoid damage of the detector.

Conventionally, a charging port of a detector may be disposed on a side of the detector. When the detector placed in a detector box needs to be charged, a charging connector of a charger may be moved into the detector box manually by a user. After the detector is charged, the charging connector of the charger needs to be taken out from the detector box manually by a user. This charging approach is not only poorly experienced, but also easy to damage the detector box. In order to facilitate the charging of the detector, the present disclosure provides a detector box including a charging assembly. The charging assembly may be arranged on a housing of the detector box. In some embodiments, the charging assembly may include a charging head. After the detector is placed into the detector box, the detector may be charged with the charging head. In order to avoid that the charging connector of the charger needs to be taken out from the detector box manually by a user after the charging of the detector is finished, in some embodiments, the charging assembly may also include an elastic element. The elastic element may be configured to drive the charging head away from the charging port of the detector.

In some embodiments, the detector box may include a panel. The panel may be connected to a first end of the housing. The housing may have a closed state (also referred to as a closed state of the detector box 40) in which at least a portion of an insertion opening of the housing may be covered by the panel and an open state (also referred to as an open state of the detector box 40) in which the housing may be angled to the panel. In some embodiments, in order to make the detector placed in the detector box automatically connect with the charging head, the detector box may also include a driving unit arranged on the panel. The driving unit may be configured to drive the charging head to overcome an elastic force of the elastic element to move into the accommodating cavity and be plugged into the charging port when the housing is switched from the open state to the closed state. More descriptions for the detector box may be found elsewhere in the present disclosure. See, e.g., FIGS. 4-7 and relevant descriptions thereof.

Figure 4:
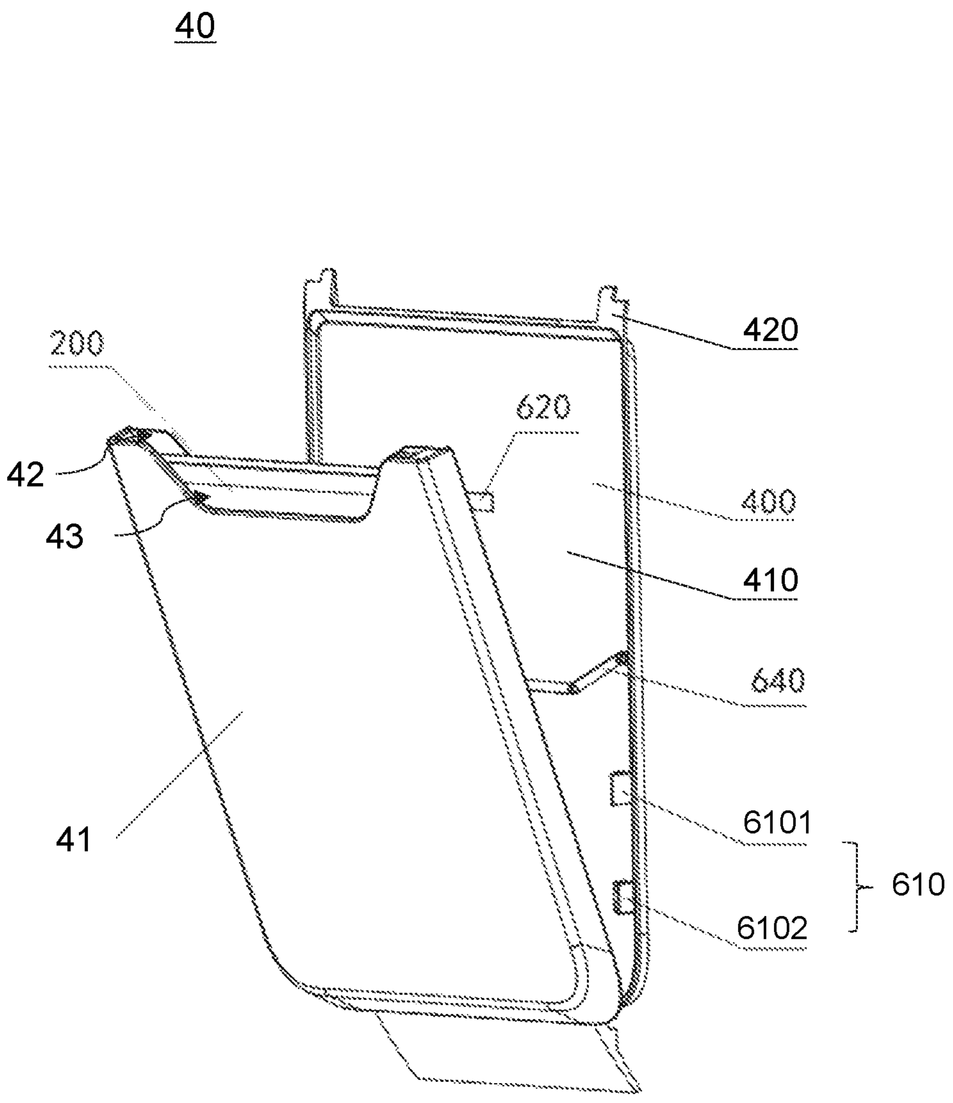
FIG. 4 is a schematic diagram illustrating an exemplary detector box according to some embodiments of the present disclosure.
Figure 5:
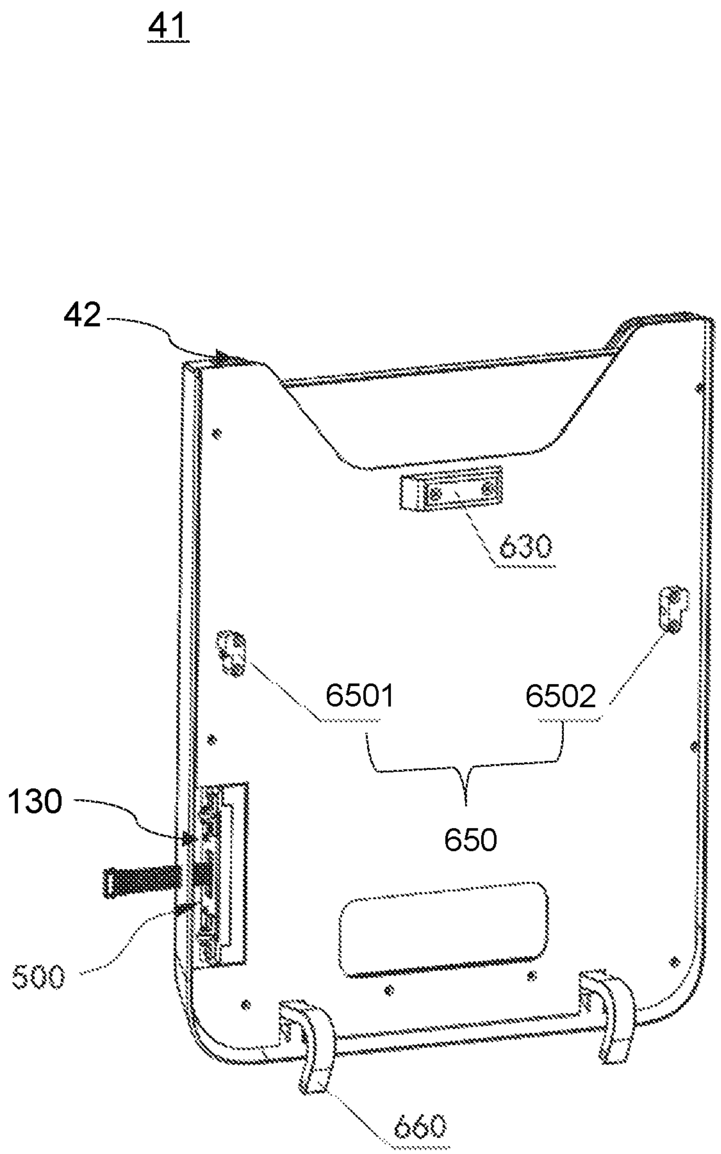
FIG. 5 is a schematic diagram illustrating an exemplary housing of the detector box in FIG. 4 according to some embodiments of the present disclosure.

FIG. 4 is a schematic diagram illustrating an exemplary detector box 40 according to some embodiments of the present disclosure. FIG. 5 is a schematic diagram illustrating an exemplary housing 41 of the detector box 40 in FIG. 4 according to some embodiments of the present disclosure. As shown in FIG. 4 and FIG. 5, the detector box 40 may include a housing 41, a panel 400, a charging assembly 500, and a driving unit 610. The housing 41 may be a main structure for accommodating a detector 200 (e.g., a flat panel detector). Since the detector 200 is generally a cuboid structure, the housing 41 may have a box-shaped structure with a cuboid accommodating cavity. An insertion opening 42 may be arranged on a side wall of the housing 41 with a smaller size. Alternatively, the insertion opening 42 may be arranged on a side wall of the housing 41 with a larger size. The insertion opening 42 may be configured to allow insertion of the detector 200 into the accommodating cavity. In order to facilitate taking out the detector 200 from the accommodating cavity, a downwardly recessed groove 43 may be arranged on the insertion opening 42. A portion of the detector 200 may be exposed outside the groove 43, so that a user may directly control the exposed part of the detector 200 to take the detector 200 out of the accommodating cavity.

In some embodiments, the insertion opening 42 may be disposed on a second end (e.g., an upper end in FIG. 4) of the housing 41, and a first end (e.g., a lower end in FIG. 4) of the housing 41 opposite to the second end of the housing 41 may be movably connected to the panel 400 (e.g., via a hinge 660). In some embodiments, the first end (e.g., the lower end in FIG. 4) of the housing 41 may be movably connected to a first end (e.g., a lower end in FIG. 4) of the panel 400 (e.g., via a hinge 660), and the second end (e.g., the upper end in FIG. 4) of the housing 41 may rotate around the hinge 660, so that the housing 41 may have a closed state in which at least a portion of the insertion opening 110 is covered by the panel 400 and an open state in which the housing 41 is angled to the pane 400. In some embodiments, when the housing 41 is in the closed state, the housing 41 may be in contact with the panel 400. In some embodiments, the first end of the housing 41 may be movably connected to the panel 400 by other components (e.g., a rotating shaft, a rotating link, etc.).

In some embodiments, the panel 400 may have a rectangular structure. A fastening groove 410 matching with the shape of the housing 41 may be arranged on the panel 400. For example, if the housing 41 has a cuboid structure, the fastening groove 410 may be a rectangular groove. When the housing 41 and the panel 400 are in the closed state, the sidewalls of the fastening groove 410 may block the insertion opening 42 to prevent the detector 200 from leaving the detector box 40. In some embodiments, one or more handles 420 may be arranged on a second end (e.g., an upper end in FIG. 4) of the panel 400. For example, as shown in FIG. 4, two handles 420 may be arranged on the second end of the panel 400. A user may exert a force on the two handles 420 to separate the panel 400 with the housing 41, so that the housing 41 is angled with the panel 400, that is, the housing 41 is in the open state.

In some embodiments, the charging assembly 500 may be disposed within the accommodating cavity of the housing 41. The charging assembly 500 may be configured to achieve the insertion and separation between a charging head and a charging port of the detector 200 in the accommodating cavity, thereby achieving powering on or powering off of the detector 200. As shown in FIG. 5, a socket opening 130 may be arranged on a surface of the housing 41 facing the panel 400. The charging assembly 500 may face the socket opening 130. The opening direction of the socket opening 130 may be perpendicular to the opening direction of the insertion opening 110. For example, as shown in FIG. 5, the plane that the insertion opening 42 locates in may be vertical to the plane that the socket opening 130 locates in. The socket opening 130 may be configured to allow a driving unit 610 disposed on the panel 400 to be in contact with the charging assembly 500. In some embodiments, as shown in FIG. 5, the charging assembly 500 may be disposed within the accommodating cavity of the housing 41, or may be disposed outside the housing 41 according to specific needs.

In some embodiments, the charging assembly 500 may include a charging head 510 and an elastic element 520. The charging head 510 may be movably disposed with respect to the housing 41. An end of the charging head 510 may be opposite to the charging port located on a side of the detector 200. The elastic element 520 may be connected to the charging head 510. The elastic element 520 may be configured to drive the charging head 510 to separate with the charging port of the detector 200. In some embodiments, the elastic element 520 may be a spring.

In some embodiments, the driving unit 610 may be arranged on the panel 400 and located on a surface of the panel 400 facing the housing 41. When the housing 41 is switched from the open state to the closed state, the driving unit 610 may drive the charging head 510 to move close to the housing 41 and be plugged into the charging port. When the housing 41 is switched from the closed state to the open state, the driving unit 610 may be gradually away from the socket opening 130, and the elastic element 520 may drive the charging head 510 to separate with the charging port of the detector 200.

In some embodiments, the detector box 40 may automatically realize the insertion of the charging head 510 into the charging port of the detector 200 when the housing 41 is in the closed state, and the separation of the charging head 510 from the charging port of the detector 200 when the housing 41 is in the open state. The user does not need to manually plug and unplug the charging head 510 when a user uses the detector box 40, which may protect the charging head 510 and the charging port, thereby prolonging the service life of the detector box 40.

Figure 6:
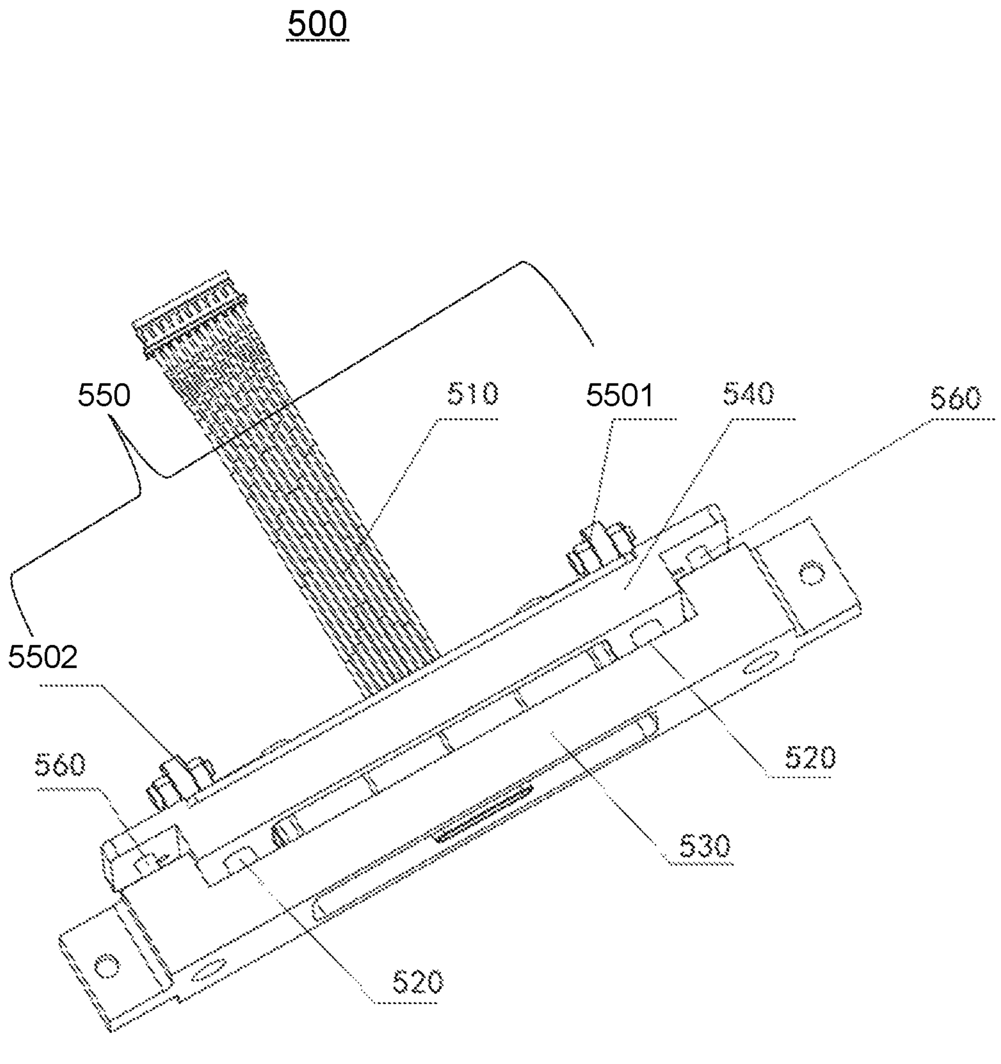
FIG. 6 is a schematic diagram illustrating an exemplary charging assembly of the detector box in FIG. 4 when the detector box is in an open state according to some embodiments of the present disclosure.
Figure 7:
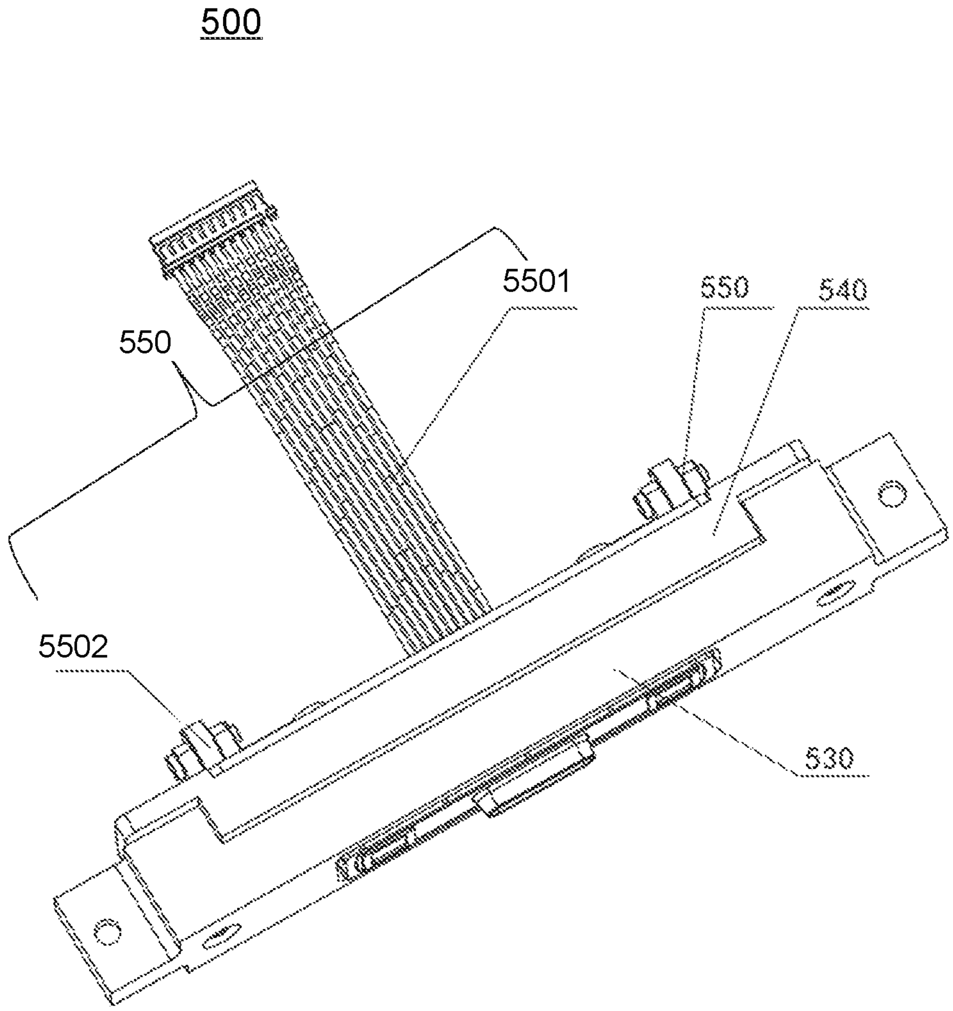
FIG. 7 is a schematic diagram illustrating an exemplary charging assembly of the detector box in FIG. 4 when the detector box is in a closed state according to some embodiments of the present disclosure.

In some embodiments, in order to provide a guide to the movement of the charging head 510 within the accommodating cavity to improve the moving accuracy of the charging head 510, as shown in FIG. 6 and FIG. 7, the charging assembly 500 may include a charging base 530 and a movable base 540. The charging base 530 may be disposed within the accommodating cavity by a screw. A charging opening may be arranged on the charging base 530 and opposite to the charging port. In some embodiments, a long side of the charging base 530 may be parallel with a long side of the housing 41. In some embodiments, a long side of the charging base 530 may be vertical to the side of the housing 41 where the insertion opening 42 locates. The movable base 540 may be arranged within the accommodating cavity and opposite to the charging base 530. The elastic element 520 may be arranged between the charging base 530 and the movable base 540. One end of the elastic element 520 may be connected to the charging base 530, and another end of the elastic element 520 may be connected to the movable base 540.

In some embodiments, the charging head 510 may be connected to the movable base 540. When the movable base 540 move close to the driving unit 610 under an action of an external force (e.g., when a user pushes the housing 41 towards the panel 400 to close the housing 41), the charging head 510 may move to the charging base 530 synchronously. An end of the charging head 510 may be plugged into the charging port through the charging opening, during which the elastic element 520 is gradually compressed. The charging opening may provide a guiding action for the movement of the charging head 510 to improve the accuracy of the movement of the charging head 510, thereby avoiding that the charging head 510 cannot be plugged into the charging port. When the driving unit 610 is away from the socket opening 130, the compressed elastic element 520 may release the elastic potential energy, so that the movable base 540 may automatically move away from the charging base 530 to achieve the disconnection of the charging head 510 and the charging port.

In some embodiments, the charging assembly 500 may include a guiding component. The guiding component may be configured to guide a movement of the movable base 540 relative to the charging base 530. Specifically, in some embodiments, the guiding component may be a guidepost 560 disposed between the charging base 530 and the movable base 540. In some embodiments, one end of the guidepost 560 may be fixed to the charging base 530 and another end of the guidepost 560 may pass through a guide hole arranged on the movable base 540. When the movable base 540 moves close to the charging base 530, the guidepost 560 may move along the guide hole to provide a guide to the movement of the movable base 540 and the movement of the charging head 510 fixed to the movable base 540, thereby improving the accuracy of the movement of the charging head 510. In some embodiments, the guide hole may be arranged on the charging base 530. One end of the guidepost 560 may be connected to the movable base 540, and another end of the guidepost 560 may pass through the guide hole. The guidepost 560 may include one or more guiding members. For example, the guidepost 560 may include two guiding members arranged between the charging base 530 and the movable base 540 at intervals.

In some embodiments, in order to reduce the size of the charge assembly 500, and further improve the accuracy of the movement of the movable base 540, as shown in FIG. 6 and FIG. 7, the charging base 530 may have a structure similar to a U-shape. A surface of the charging base 530 facing the movable base 540 may include a first end surface, a second end surface, and a third end surface that are sequentially connected in a fold line. The first end surface and the third end surface may be located in a same first plane. The second end surface may be located in a second plane that is parallel to the first plane. The second end surface may be connected with the first end surface and the third end surface through two side surfaces, so that the second end surface is a concave surface relative to the first end surface and the third end surface. The movable base 540 have a structure similar to a T-shape that matches with the structure similar to a U-shape of the charging base 530. A surface of the movable base 540 facing the charging base 530 may include a fourth end, a fifth end surface, and a sixth end surface that are sequentially connected in a fold line. The fourth end surface and the sixth end surface may be located in a same third plane. The fifth end surface may be located in a fourth plane that is parallel to the third plane. The fifth end surface may be connected with the fourth end surface and the sixth end surface through two side surfaces, so that the fifth end surface is a convex surface relative to the fourth end surface and the sixth end surface. The movable base 540 may be tightly spliced with the charging base 530 under an action of the driving unit 610, so that the first end surface is fitted with the fourth end surface, the second end surface is fitted the fifth end surface, and the third end surface is fitted the sixth end surface, respectively.

In some embodiments, the two guiding members of the guidepost 560 may be disposed between the first end surface and the fourth end surface, and between the third end surface and the sixth end surface, respectively. The elastic element 520 may be disposed between the second end surface and the fifth end surface. In this way, the size of the charging assembly 500 may be reduced.

In some embodiments, in order to facilitate the driving unit 610 to drive the movable base 540, a guide roller 550 may be arranged on one end of the movable base 540 away from the charging base 530. In some embodiments, the guide roller 550 may be rotatably connected to the movable base 540 via a rotating base and a rotating shaft. When the driving unit 610 enters the socket opening 130, the driving unit 610 may abut against the guide roller 550, so that the guide roller 550 may drive the movable base 540 to move to the charging base 530. The guide roller 550 may reduce the friction between the driving unit 610 and the movable base 540, thereby reducing the difficulty of the drive to improve the smoothness of the drive. In some embodiments, the driving unit 610 may be provided with a driving inclined surface configured to abut against the movable base 540. The driving inclined surface may abut against the guide roller 550. The driving inclined surface can make the driving unit 610 easy to enter the socket opening 130 to abut against the guide roller 550, and capable of moving the movable base 540 to the charging base 530 to improve the stability of the movement. In some embodiments, the movable base 540 may be provided with a guiding inclined surface, and the driving inclined surface may be configured to abut against the guiding inclined surface.

In some embodiments, the guide roller 550 may include a plurality of guide members and the driving unit 610 may include a plurality of driving elements. Each of the plurality of guide members may correspond to one of the plurality of driving elements. In some embodiments, the plurality of guide members may be arranged on the movable base 540 at intervals. For example, as shown in FIG. 4, FIG. 6, and FIG. 7, the guide roller 550 may include two guide members 5501 and 5502 and the driving unit 610 may include two driving elements 6101 and 6102. The two guide members 5501 and 5502 may be arranged on the movable base 540, and the two driving elements 6101 and 6102 may be arranged on the panel 400. By this way, the stability of the movement of the movable base 540 may be improved.

In some embodiments, in order to support the detector 200 and adjust a viewing angle of the detector 200 or an angle between the panel 400 and the housing 41 to improve user experience. A limit mechanism may be arranged between the housing 41 and the panel 400. The limit mechanism may be configured to limit the angle between the panel 400 and the housing 41 in the open state. In some embodiments, as shown in FIG. 4 and FIG. 5, the limit mechanism may include a movable rod 640 and a rod base 650. The rod base 650 may be arranged on the housing 41. A first end of the movable rod 640 may be rotatably connected to the panel 400, and a second end of the movable rod 640 may be connected to the rod base 650. In some embodiments, the movable rod 640 may be a U-shaped rod. The U-shaped rod may include a first rod (e.g., a vertical rod), a second rod (e.g., a vertical rod), and a third rod (e.g., a horizontal rod). The third rod may be located between the first rod and the second rod, and connect the first rod and the second rod. Two free ends of the first rod and the second rod of the U-shaped rod may be rotatably connected to the panel 400, and the third rod of the U-shaped rod may be hooked on the rod base 650. In some embodiments, the rod base 650 may include a plurality of base members. For example, as shown in FIG. 5, the rod base 650 may include two base members 6501 and 6502 arranged on the housing 41 at intervals to improve the stability of the connection.

In some embodiments, the limit mechanism may include a rope. In some embodiments, a first end of the rope may be connected to the panel 400, and a second end of the rope may be connected to the housing 41. Alternatively, two ends of the rope may be connected to the panel 400, and a portion (e.g., the middle portion) between the two ends of the rope may be hooked on the housing 41. In some embodiments, the rope may include a wire rope.

In some embodiments, in order to the stability of the detector box 40 in the closed state, an attraction component may be arranged between the housing 41 and the panel 400. In some embodiments, the attraction component may include a first attraction element 620 and a second attraction element 630. The first attraction element 620 may be arranged on the panel 400, and the second attraction element 630 may be arranged on the housing 41. The first attraction element 620 and the second attraction element 630 may be attracted together when the housing 41 is in the closed state, so that the housing 41 and the panel 400 may be stably fastened together. In some embodiments, the first attraction element 620 may be a metal, and the second attraction element 630 may be a magnet. In some embodiments, the first attraction element 620 may be a magnet, and the second attraction element 630 may be a metal. In some embodiments, the first attraction element 620 and the second attraction element 630 may be magnets with opposite magnetism. In some embodiments, the first attraction element 620 and the second attraction element 630 may be electromagnets. Induction switches may be arranged on the electromagnets. When a user trying to open the panel 400 is detected, the induction switches may send a signal to de-energize the electromagnets, so that the panel 400 may be easily opened. In some embodiments, the electromagnets may be connected to an external power source. When a hand of a user is close to the detector box 40 and ready to pull the panel 400, the external power source may power off to the electromagnets according to the signal sent by the induction switches, so that the electromagnets lose suction. Exemplary external power sources may include a battery, a mobile X-ray device, or the like. Exemplary induction switches may include an infrared pyroelectric sensor, a photoelectric switch, or the like. In some embodiments, the induction switches may be piezoelectric sensors mounted within the handle 420. When a hand of the user controls the handle 420 and prepares to pull the panel 400, the piezoelectric sensors may send a signal to make the electromagnets to lose suction, so that the user may easily pull the panel 400.

Yet another aspect of the present disclosure provides a detector. The detector may be accommodated and protected using the detector box 40 of the present disclosure. Yet another aspect of the present disclosure provides a mobile X-ray device configured to perform X-ray imaging to an object (e.g., a patient). The mobile X-ray device may include an X-ray source configured to emit X-rays and a detector (e.g., a flat panel detector) configured to receive the X-rays emitted from the X-ray source. The mobile X-ray device may be provided with a detector box 40 of the present disclosure configured to accommodate and protect the detector when the detector is not in a working state. In some embodiments, the housing 41 may be fixed on the mobile X-ray device. A user may pull the panel 400 to make the panel 400 away from the housing 41, so as to open the detector box 40, and push the panel 400 to make the panel 400 close to the housing 41, so as to close the detector box 40. In some embodiments, the panel 400 may be fixed on the mobile X-ray device. A user may pull the housing 41 to make the housing 41 away from the panel 400, so as to open the detector box 40, and push the housing 41 to make the housing 41 close to the panel 400, so as to close the detector box 40. In some embodiments, the mobile X-ray device may include a mobile digital radiography (DR) device, a mobile digital subtraction angiography (DSA) device, or a mobile C-arm device.

In some embodiments, the present disclosure also provide a detector box that is a combination of the detector box 10 and the detector box 40. In some embodiments, the locking mechanism 300 illustrated in FIGS. 1 through 3 may be applied in the detector box 40 illustrated in FIGS. 4 through 7.

In some embodiments, when the detector box 40 is in an open state, which indicates that the detector 200 may be required to be taken out from the detector box 40, the locking mechanism 300 may be in an unlocked state to allow the detector 200 to be taken out from the detector box 40. When the detector box 40 is in a closed state, which indicates that the detector 200 may be required to be inside the detector box 40, the locking mechanism 300 may be in a locked state to prevent the detector 200 from leaving the detector box 40.

In some embodiments, a force sensor may be disposed on the first attraction element 620 and/or the second attraction element 630. When the detector box 40 is in the open state, the housing 41 may be separated with the panel 400, so that the first attraction element 620 may be separated with the second attraction element 630. The force sensor may detect the variation of the attraction force between the first attraction element 620 and the second attraction element 630. When the force sensor detects that the attraction force between the first attraction element 620 and the second attraction element 630 disappears, the force sensor may output a signal to the external power source (e.g., a mobile X-ray device) of the magnetic element 344. After the external power source receives the signal, the external power source may energize the magnetic element 344, so that the locking mechanism 300 may be in the unlocked state to allow the detector 200 to be taken out from the detector box 40. When the detector box 40 is in the closed state, the housing 41 may be in contact with the panel 400, so that the first attraction element 620 and the second attraction element 630 may be attracted together. When the force sensor detects an attraction force between the first attraction element 620 and the second attraction element 630, the force sensor may output a signal to the external power source (e.g., a mobile X-ray device) of the magnetic element 344. After the external power source receives the signal, the external power source may power off the magnetic element 344 to allow the locking block 310 to rotate.

In some embodiments, a sensor may be disposed to detect the electrical signals of the charging assembly 500. When the detector box 40 is in the open state, the charging head of the charging assembly 500 may be plugged into the charging port of the detector 200 to charge the detector 200. When the sensor detects electrical signals in the charging assembly 500, the sensor may output a control signal to the external power source (e.g., a mobile X-ray device) of the magnetic element 344. After the external power source receives the control signal, the external power source may energize the magnetic element 344, so that the locking mechanism 300 may be in the unlocked state to allow the detector 200 to be taken out from the detector box 40. When the detector box 40 is in the closed state, the charging head of the charging assembly 500 may be separated with the charging port of the detector 200. When the sensor detects that electrical signals in the charging assembly 500 disappears, the sensor may output a control signal to the external power source (e.g., a mobile X-ray device) of the magnetic element 344. After the external power source receives the signal, the external power source may power off the magnetic element 344 to allow the locking block 310 to rotate.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification or determination is provided for illustration purposes and modified according to different situations. For example, a classification condition that "a value is greater than the threshold value" may further include or exclude a condition that "the probability value is equal to the threshold value."

What is claimed is:

1. A device, comprising:

a housing including an accommodating cavity and an insertion opening configured to allow insertion of a detector into the accommodating cavity;

a locking mechanism configured to prevent the detector from leaving the accommodating cavity; and a charging assembly arranged on the housing, the charging assembly including a charging head and an elastic element configured to drive the charging head away from a charging port of the detector.

2. The device of claim 1, wherein the locking mechanism is arranged on one end of the insertion opening; and a locking block is arranged on a first end of the locking mechanism close to the insertion opening, and a second end of the locking mechanism away from the insertion opening is configured to be lockable, so that the locking block has a locked state that prevents the detector from leaving the accommodating cavity.

3. The device of claim 1, further comprising:

a panel connected to a first end of the housing, the housing having a closed state in which the housing is in contact with the panel and an open state in which the housing is angled to the panel;

a driving unit arranged on the panel, the driving unit being configured to drive the charging head to overcome an elastic force of the elastic element to move into the accommodating cavity and be plugged into the charging port when the housing is switched from the open state to the closed state.

4. The device of claim 3, wherein the charging assembly includes a charging base and a movable base, wherein:

a charging opening is arranged on the charging base and opposite to the charging port;

the movable base is opposite to the charging base, the elastic element being arranged between the charging base and the movable base;

the charging head is connected to the movable base; and the movable base is configured to drive, under an action of the driving unit, the charging head to be plugged into the charging port through the charging opening.

5. The device of claim 4, wherein the charging assembly includes a guiding component configured to guide a movement of the movable base relative to the charging base.

6. The device of claim 4, wherein the driving unit is provided with a driving inclined surface abutting against the movable base.

7. The device of claim 3, wherein:

the charging assembly includes a movable base, the driving unit is provided with a driving inclined surface abutting against the movable base, and a guide roller is rotatably arranged on the movable base, the driving inclined surface abutting against the guide roller.

8. The device of claim 3, wherein the charging assembly includes a movable base, the driving unit is provided with a driving inclined surface, and the movable base is provided with a guiding inclined surface, the driving inclined surface of the driving unit abutting against the guiding inclined surface.

9. The device of claim 3, wherein a first attraction element is arranged on the panel, and a second attraction element is arranged on the housing, wherein:

the first attraction element and the second attraction element are attracted together when the housing is in the closed state.

10. The device of claim 9, wherein:

the first attraction element and the second attraction element are magnets; or one of the first attraction element and the second attraction element is metal, and another of the first attraction element and the second attraction element is a magnet; or the first attraction element and the second attraction element are electromagnets, induction switches being arranged on the electromagnets, the induction switches being configured to de-energize the electromagnets when an object is detected.

11. The device of claim 3, wherein a limit mechanism is arranged between the housing and the panel, the limit mechanism being configured to limit an angle between the panel and the housing in the open state.

12. The device of claim 11, wherein the limit mechanism includes a movable rod and a rod base, wherein:

the rod base is arranged on the housing; and a first end of the movable rod is rotatably connected to the panel, and a second end of the movable rod is connected to the rod base.

13. A device, comprising:

a housing including an accommodating cavity and an insertion opening configured to allow insertion of a detector into the accommodating cavity;

a panel connected to a first end of the housing, the housing having a closed state in which the housing is in contact with the panel and an open state in which the housing is angled to the panel;

a charging assembly arranged on the housing, the charging assembly including a charging head and an elastic element configured to drive the charging head away from a charging port of the detector; and a driving unit arranged on the panel, the driving unit being configured to drive the charging head to overcome an elastic force of the elastic element to move into the accommodating cavity and be plugged into the charging port when the housing is switched from the open state to the closed state.

14. A device, comprising:

a housing including an accommodating cavity and an insertion opening configured to allow insertion of a detector into the accommodating cavity;

a locking mechanism configured to prevent the detector from leaving the accommodating cavity and arranged on one end of the insertion opening, wherein:

a locking block is arranged on a first end of the locking mechanism close to the insertion opening, and a second end of the locking mechanism away from the insertion opening is configured to be lockable, so that the locking block has a locked state that prevents the detector from leaving the accommodating cavity.

15. The device of claim 14, wherein the locking mechanism includes a driving rod and a locking assembly, wherein:

the driving rod is rotatably connected to the housing via a rotating shaft;

the locking block is arranged on a first end of the driving rod, and a locking groove is arranged on a second end of the driving rod; and the locking assembly has a locked state in which the locking groove is connected with the locking assembly and an unlocked state in which the locking assembly is separated from the locking groove.

16. The device of claim 15, wherein the locking assembly includes a telescopic shaft and a driving component, and the driving component is configured to drive the telescopic shaft to move close to or away from the locking groove.

17. The device of claim 16, wherein the driving component includes:

a magnetic element configured to drive the telescopic shaft to move away from the locking groove when the magnetic element is energized; and a first elastic member, one end of the first elastic member being connected with the telescopic shaft, the first elastic member being configured to drive the telescopic shaft to move close to the locking groove when the magnetic element is powered off.

18. The device of claim 15, wherein the locking mechanism includes a second elastic member, a first end of the second elastic member being connected to the housing, and a second end of the second elastic member being connected to the driving rod, so that the locking block has an initial state that allows the detector to leave the accommodating cavity.

19. The device of claim 18, wherein the second end of the second elastic member is connected to a portion of the driving rod between the rotating shaft and the locking groove to tighten the second end of the driving rod away from the locking block, so that the locking block is driven to move away from the detector.

20. The device of claim 18, wherein the second end of the second elastic member is connected to a portion of the driving rod between the rotating shaft and the locking block to drive the locking block to move away from the detector.

* * * * *